United States Patent [19]
Uhling

[11] Patent Number: 6,028,320
[45] Date of Patent: Feb. 22, 2000

[54] DETECTOR FOR USE IN A PRINTING DEVICE HAVING PRINT MEDIA WITH FLUORESCENT MARKS

[75] Inventor: Thomas F Uhling, Vancouver, Wash.

[73] Assignee: Hewlett-Packard Company, Palo Alto, Calif.

[21] Appl. No.: 09/009,800

[22] Filed: Jan. 20, 1998

[51] Int. Cl.[7] .................................................. G01N 21/86
[52] U.S. Cl. .............................. 250/559.44; 250/458.1; 399/84
[58] Field of Search ............................. 250/559.44, 557, 250/235, 458.1; 399/84; 355/112

[56] References Cited

U.S. PATENT DOCUMENTS

| | | | |
|---|---|---|---|
| 4,340,663 | 7/1982 | Mikawa et al. | 430/496 |
| 4,503,323 | 3/1985 | Flam | 235/489 |
| 4,641,019 | 2/1987 | Inatsuki | 250/559.02 |
| 4,734,868 | 3/1988 | DeLacy | 358/1.12 |
| 4,865,478 | 9/1989 | Chan et al. | 400/616.3 |
| 4,916,638 | 4/1990 | Haselby et al. | 358/1.5 |
| 5,252,991 | 10/1993 | Storlie et al. | 347/262 |
| 5,444,469 | 8/1995 | Cowger | 347/14 |
| 5,484,994 | 1/1996 | Roustaei | 235/462.25 |
| 5,523,562 | 6/1996 | Maple | 250/235 |
| 5,568,172 | 10/1996 | Cowger | 347/19 |
| 5,668,363 | 9/1997 | Nishida et al. | 235/468 |
| 5,770,841 | 6/1998 | Moed et al. | 235/375 |
| 5,821,523 | 10/1998 | Bunte et al. | 235/472.01 |
| 5,877,486 | 3/1999 | Maltsev et al. | 235/462.15 |
| 5,880,176 | 3/1999 | Kamoto et al. | 523/172 |

*Primary Examiner*—Que T. Le
*Assistant Examiner*—Thanh X. Luu
*Attorney, Agent, or Firm*—Erik A. Anderson

[57] ABSTRACT

A detector for use in detecting at least one mark on a sheet of print media used in a printing device, the mark indicating at least one characteristic of the sheet of print media, is disclosed. The detector includes a source, a sensor, and a bandstop filter. The source generates a first light signal that is directed at the mark on the sheet of print media, the first light signal having a first predetermined wavelength. The sensor is configured to detect a second light signal from the mark on the sheet of print media, the second light signal arising in response to the first light signal and having a second predetermined wavelength. The bandstop filter is positioned between the sensor and the mark on the sheet of print media and is configured to block from the sensor the first predetermined wavelength of the first light signal generated by the source and transmit to the sensor other wavelengths of light, including the second predetermined wavelength of the second light signal. A printing device including the detector is also disclosed. A method of detecting a characteristic of a sheet of print media used in a printing device through the use of a detector is also disclosed. Further characteristics and features of the detector and printing device are described herein. Further characteristics and steps of the method are also described herein.

19 Claims, 7 Drawing Sheets

DETECTOR FOR USE IN A PRINTING DEVICE HAVING PRINT MEDIA WITH FLUORESCENT MARKS

BACKGROUND AND SUMMARY

The present invention relates to printing devices. More particularly, the present invention relates to a detector having a bandstop filter that allows the detector to detect at least one characteristic of a sheet of print media used in a printing device and also to detect visible inks used in the printing device.

Printing devices, such as inkjet printers, use printing composition (e.g., ink or toner) to print text, graphics, images, etc. onto print media The print media may be of any of a variety of different types. For example, the print media may include paper, transparencies, envelops, photographic print stock, cloth, etc. Each of these types of print media has various characteristics that ideally should be accounted for during printing, otherwise a less than optimal printed output may occur. Additionally, various print media factors may affect print quality, including print media size and print media orientation.

One way in which a printing device can be configured to a particular print media is to have a user make manual adjustments to the printing device based upon these characteristics and factors. One problem with this approach is that it requires user intervention which is undesirable. Another problem with this approach is that it requires a user to correctly identify various characteristics of a particular print media. A further problem with this approach is that a user may incorrectly manually configure the printing device so that optimal printing still does not occur in spite of user intervention. A device and method for automatically detecting the different characteristics and factors of various print media used in a printing device would be a welcome improvement.

In addition to accounting for particular media types, there are various operating parameters of a printing device that must be initialized and monitored to help achieve optimal printing. These parameters depend upon the type of printing device being used. For example, with inkjet printing devices some of these parameters include alignment of a black ink cartridge with one or more color ink cartridges, detection of clogged printhead nozzles, ink drop volume measurement, and bi-directional printing alignment.

A device and method for initializing and monitoring various operating parameters of a printing device to help achieve optimal printing would also be a welcome improvement. One way in which these various tasks could be accomplished for inkjet printing is through the use of a optical detector that includes a sensor configured to detect visible inks used in the printing device. Such a device would be designed to transmit data acquired by this detection to a controller or other similar device which utilizes this data in managing operation of the inkjet printing device.

Ideally, both of these above-described devices could be integrated into a single detector to conserve space and potentially save cost. Accordingly, the present invention is directed at providing a single detector that is designed to help optimize printing on a variety of different types of print media, under a variety of operating conditions and user inputs, and to detect visible inks used in the printing device.

An embodiment of a detector in accordance with the present invention for use in detecting at least one mark on a sheet of print media used in a printing device, the mark indicating at least one characteristic of the sheet of print media, includes a source, a sensor, and a bandstop filter. The source generates a first light signal that is directed at the mark on the sheet of print media. The first light signal has a first predetermined wavelength. The sensor is configured to detect a second light signal from the mark on the sheet of print media. The second light signal arises in response to the first light signal and has a second predetermined wavelength. The bandstop filter is positioned between the sensor and the mark on the sheet of print media. The bandstop filter is configured to block from the sensor the first predetermined wavelength of the first light signal generated by the source and transmit to the sensor other wavelengths of light, including the second predetermined wavelength of the second light signal.

The above-described detector may be modified and include the following characteristics described below. The first light signal may have a first range of predetermined wavelengths and the second light signal may have a second range of predetermined wavelengths. In such cases, the bandstop filter is configured to block from the sensor the first range of predetermined wavelengths of the first light signal and transmit other wavelengths of light to the sensor, including the second range of predetermined wavelengths of the second light signal. The first range of wavelengths may be substantially between 610 nanometers and 700 nanometers. The second range of wavelengths may be substantially between 675 nanometers and 1,000 nanometers.

The detector may be used in a printing device.

A printing device in accordance with the present invention includes a sheet of print media, a printing mechanism, a controller, and a detector. The sheet of print media has at least one mark thereon that indicates a characteristic of the sheet of print media. This mark fluoresces at a second predetermined wavelength of light in response to absorption of a first light signal of a first predetermined wavelength. The printing mechanism is used for printing on the sheet of print media. The controller controls operation of the printing mechanism. The detector detects fluorescing of the mark on the sheet of print media and transmits in response to this detection data indicative of this mark to the controller. The detector includes a bandstop filter that is configured to block the first predetermined wavelength of the first light signal and to transmit other wavelengths of light, including the second predetermined wavelength of the second light signal. The controller is configured to utilize this data as a factor in controlling operation of the printing mechanism.

The above-described printing device may be modified and include the following characteristics described below. The first light signal may have a first range of predetermined wavelengths and the second light signal may also have a second range of predetermined wavelengths. In such cases, the bandstop filter is configured to block the first range of predetermined wavelengths of the light signal and transmit other wavelengths of light, including the second range of predetermined wavelengths of the second light signal. The first range of wavelengths may be substantially between 610 nanometers and 700 nanometers. The second range of wavelengths may be substantially between 675 nanometers and 1000 nanometers.

The first light signal may be transmitted by the detector.

An alternative embodiment of a detector in accordance with the present invention for use in detecting at least one mark on a sheet of print media used in a printing device, the mark indicating at least one characteristic of the sheet of print media, includes structure for generating a first light signal that is directed at the mark on the sheet of print media, the first light signal having a first predetermined wavelength. The detector also includes structure for detecting a second light signal from the mark on the sheet of print media, the second light signal arising in response to the first signal and having a second predetermined wavelength. The detector additionally includes structure, positioned between the structure for detecting and the mark on the sheet of print media, for blocking from the structure for detecting the first predetermined wavelength of the first light signal and for transmitting to the structure for detecting other wavelengths of light, including the second predetermined wavelength of the second light signal, thereby allowing wavelengths of light other than the first wavelength of light to remain available for tasks other than detecting the mark on the sheet of print media.

The above-described detector may be modified and include the following characteristics described below. The first light signal may have a first range of predetermined wavelengths and the second light signal may have a second range of predetermined wavelengths. In such cases, the structure for blocking and transmitting is configured to block from the structure for detecting the first range of predetermined wavelengths of the first light signal and transmit to the structure for detecting other wavelengths of light, including the second range of predetermined wavelengths of the second light signal. The first range of wavelengths may be substantially between 610 nanometers and 700 nanometers. The second range of wavelengths may be substantially between 675 nanometers and 1000 nanometers.

The structure for blocking and transmitting may include a bandstop filter positioned between the structure for detecting and the mark on the sheet of print media. The first light signal may have a first range of predetermined wavelengths and the second light signal may also have a second range of predetermined wavelengths. In such cases, the bandstop filter is configured to block from the structure for detecting the first range of predetermined wavelengths of the first light signal and transmit other wavelengths of light to the structure for detecting, including the second range of predetermined wavelengths of the second light signal. The first range wavelengths may be substantially between 610 nanometers and 700 nanometers. The second range of wavelengths may be substantially between 675 nanometers and 1000 nanometers.

The structure for generating may include a light emitting diode and the means for detecting may include an optical detector.

The detector may be used in a printing device, like that described above.

An embodiment of a method in accordance with the present invention of detecting a characteristic of a sheet of print media used in a printing device through the use of a detector includes the step of generating a first light signal that is directed at the mark on the sheet of print media. The first signal has a first predetermined wavelength. The method also includes the step of fluorescing a second light signal in response to absorption of the first light signal. The second light signal has a second predetermined wavelength. The method additionally includes the steps of blocking the first predetermined wavelength of the first light signal from a sensor of the detector and transmitting other wavelengths of light to the sensor, including the second predetermined wavelength of the second light signal. The method further includes the step of detecting the second light signal fluoresced by the mark on the sheet of print media.

The above-described method may be modified and include the additional steps described below. The first light signal may have a first range of predetermined wavelengths and the second light signal may have a second range of predetermined wavelengths. In such cases, the blocking step includes blocking the first range of predetermined wavelengths of the first light signal. In such cases, the transmitting step also includes transmitting other wavelengths of light, including the second range of predetermined wavelengths of the second light signal.

The method may include the additional steps of transmitting data indicative of detection of the mark to the printing device and utilizing this data as a factor in controlling operation of the printing device.

Other objects, advantages, and novel features of the present invention will become apparent from the following detailed description of the invention when considered in conjunction with the accompanying drawings.

DETAILED DESCRIPTION OF THE DRAWINGS

Figure 1:
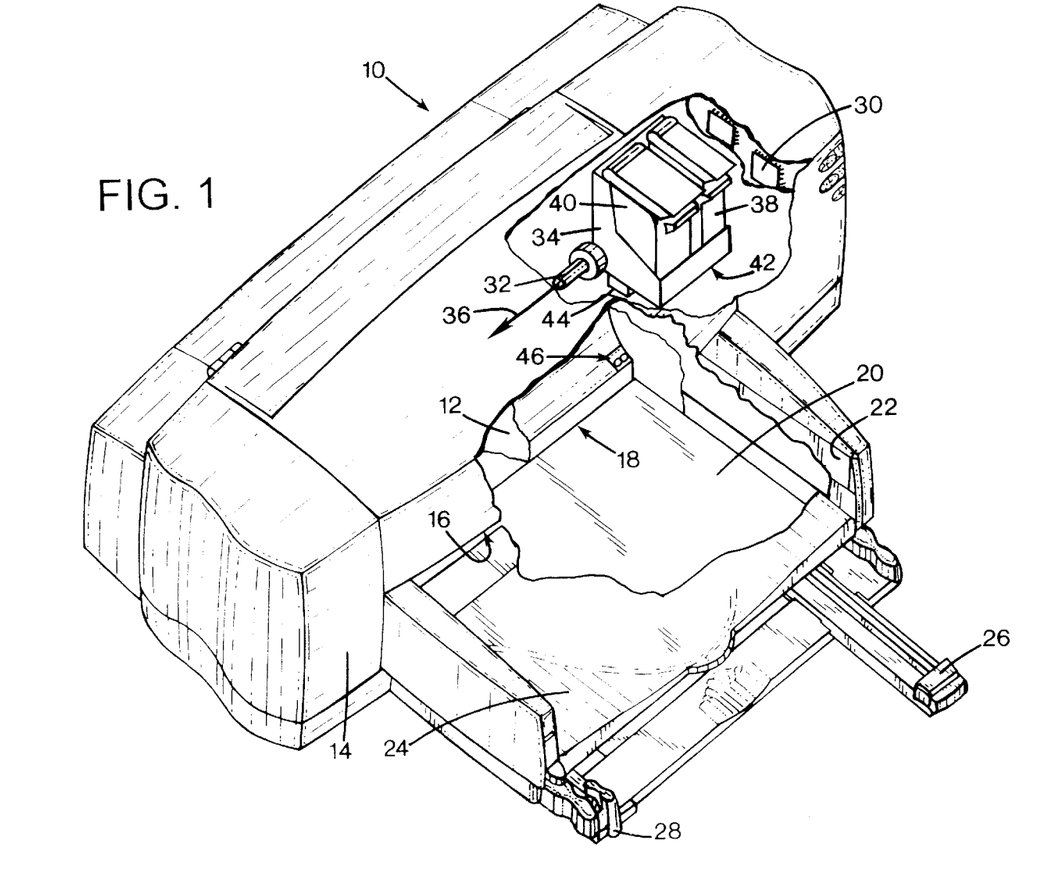
FIG. 1 is a perspective view of a printing device that includes an embodiment of a detector in accordance with the present invention.

FIG. 1 illustrates an embodiment of an printing device, here shown as an inkjet printer 10, which may be used for printing business reports, correspondence, desktop publishing, and the like, in an industrial, office, home or other environment. A variety of inkjet printing devices are commercially available. For instance, some of the printing devices that may embody the present invention, described below, include plotters, portable printing units, copiers, cameras, video printers, laser printers, and facsimile machines, to name a few. For convenience, the concepts of the present invention are illustrated in the environment of an inkjet printer 10. It is to be understood, however, that the present invention may be used in other printing devices as well, such as those described above.

While it is apparent that the printer components may vary from model to model, the typical inkjet printer 10 includes a chassis 12 surrounded by a housing or casing enclosure 14, typically of a plastic material. Sheets of print media (not shown in FIG. 1) are fed through a print zone 16 by a print media handling system 18. The print media may be any type of suitable sheet material, such as paper, card-stock, cloth, transparencies, mylar, and the like, but, for convenience, the illustrated embodiment is described using paper as the print medium. Print media handling system 18 has a feed tray 20 for storing sheets of paper before printing. A series of conventional motor-driven print media drive rollers (not shown in FIG. 1) may be used to move the print media from tray 20 into the print zone 16 for printing. After printing, the sheet then lands on a pair of retractable output drying wing members 22, only one of which is shown in FIG. 1 in a retracted position. The wings 22 momentarily hold the newly printed sheet above any previously printed sheets still drying in an output tray portion 24 before pivotally retracting to the sides to drop the newly printed sheet into the output tray 24. The media handling system 18 may include a series of adjustment mechanisms for accommodating different sizes of print media, including letter, legal, A-4, envelopes, etc., such as a sliding length adjustment lever 26, and sliding width adjustment lever 28.

Printing device 10 also has a printer controller, illustrated schematically as a microprocessor 30, that receives instructions from a host device, typically a computer, such as a personal computer (not shown). Many of the printer controller functions may be performed by the host computer, by the electronics on board the printer, or by interactions therebetween. A monitor (not shown) coupled to the computer host may be used to display visual information to an operator, such as the printer status or a particular program being run on the host computer. Personal computers, their input devices, such as a keyboard and/or a mouse device, and monitors are all well known to those skilled in the art.

A carriage guide rod 32 is supported by chassis 12 to slideably support an inkjet carriage 34 for travel back and forth across the print zone 16 along a scanning axis 36 defined by the guide rod 32. A conventional carriage propulsion system (not shown) may be used to drive carriage 34. This conventional carriage propulsion system includes a position feedback system which communicates carriage position signals to controller 30. An example of such a carriage propulsion system is a carriage drive gear and DC motor assembly that is coupled to drive an endless belt secured in a conventional manner to carriage 34, with the motor operating in response to control signals received from printer controller 30. To provide carriage positional feedback information to printer controller 30, an optical encoder reader may be mounted to carriage 34 to read an encoder strip extending along the path of carriage travel.

In print zone 16, the print media sheet receives ink from an inkjet cartridge, such as a black ink cartridge 38 and/or a color ink cartridge 40 which are parts of the printing mechanism of printing device 10. The cartridges 38 and 40 are also often called "pens" by those in the art. The illustrated color pen 40 is a tri-color pen, although in some embodiments, a set of discrete monochrome pens may be used.

The illustrated pens 38 and 40 each include reservoirs for storing a supply of ink. The pens 38 and 40 have printheads 42 and 44, respectively, each of which has an orifice plate with a plurality of nozzles formed therethrough in a manner well known to those skilled in the art. The illustrated printheads 42 and 44 are thermal inkjet printheads, although other types of printheads may be used, such as piezoelectric printheads. The printheads 42 and 44 typically include a substrate layer having a plurality of resistors which are associated with the nozzles. Upon energizing a selected resistor, a bubble of gas is formed to eject a droplet of ink from the nozzle and onto media in the print zone 16. The printhead resistors are selectively energized in response to enabling or firing command control signals, which may be delivered by a conventional multi-conductor strip (not shown) from the controller 30 to the printhead carriage 34, and through conventional interconnects between the carriage and pens 38 and 40 to the printheads 42 and 44.

An embodiment of a detector 46 constructed in accordance with the present invention is also shown in FIG. 1. Detector 46 is used for detecting at least one characteristic of a sheet of print media used in printing device 10 and transmitting data indicative of this characteristic to controller 30, as more fully discussed below. Controller 30 is configured to utilize this data as a factor in controlling operation of the printing mechanism, as also more fully discussed below.

Figure 2:
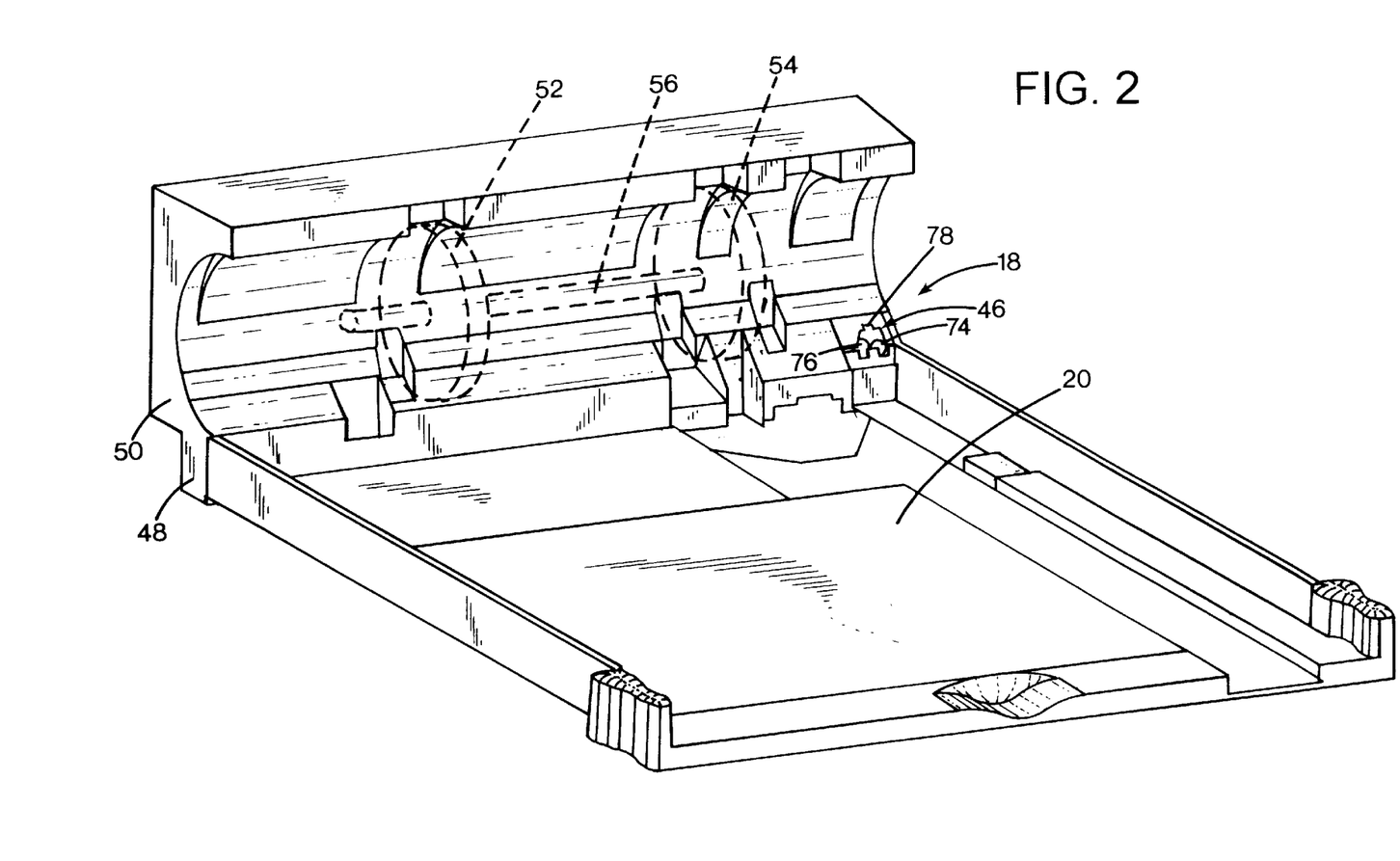
FIG. 2 is a perspective view of a print media handing system of the printing device shown in FIG. 1 and of the embodiment of the detector of the present invention shown in FIG. 1.

A perspective view of a print media handing system 18 and detector 46 is shown in FIG. 2. As can be seen in FIG. 2, print media handling system 18 includes a lower print media guide 48 and an upper print media guide 50. Print media handling system 18 also includes a pair of print media drive rollers 52 and 54 positioned adjacent lower and upper print media guides 48 and 50 and driven by a print media drive roller shaft 56. Shaft 56 is coupled to and driven by a motor, which is not shown in FIG. 2.

In operation, print media drive rollers 52 and 54 select or "pick" a sheet of media in feed tray 20 and transport the sheet of print media to print zone 16 for printing by cartridges 38 and 40 of the printing mechanism of printing device 10. During this transport, the sheet of print media moves between rollers 52 and 54 and upper and lower print media guides 48 and 50. As can be seen in FIG. 2, detector 46 of the present invention is positioned in lower print media guide 48 so that during transport of the sheet of print media to print zone 16, the sheet of print media passes over detector 46, as more fully discussed below.

Figure 3:
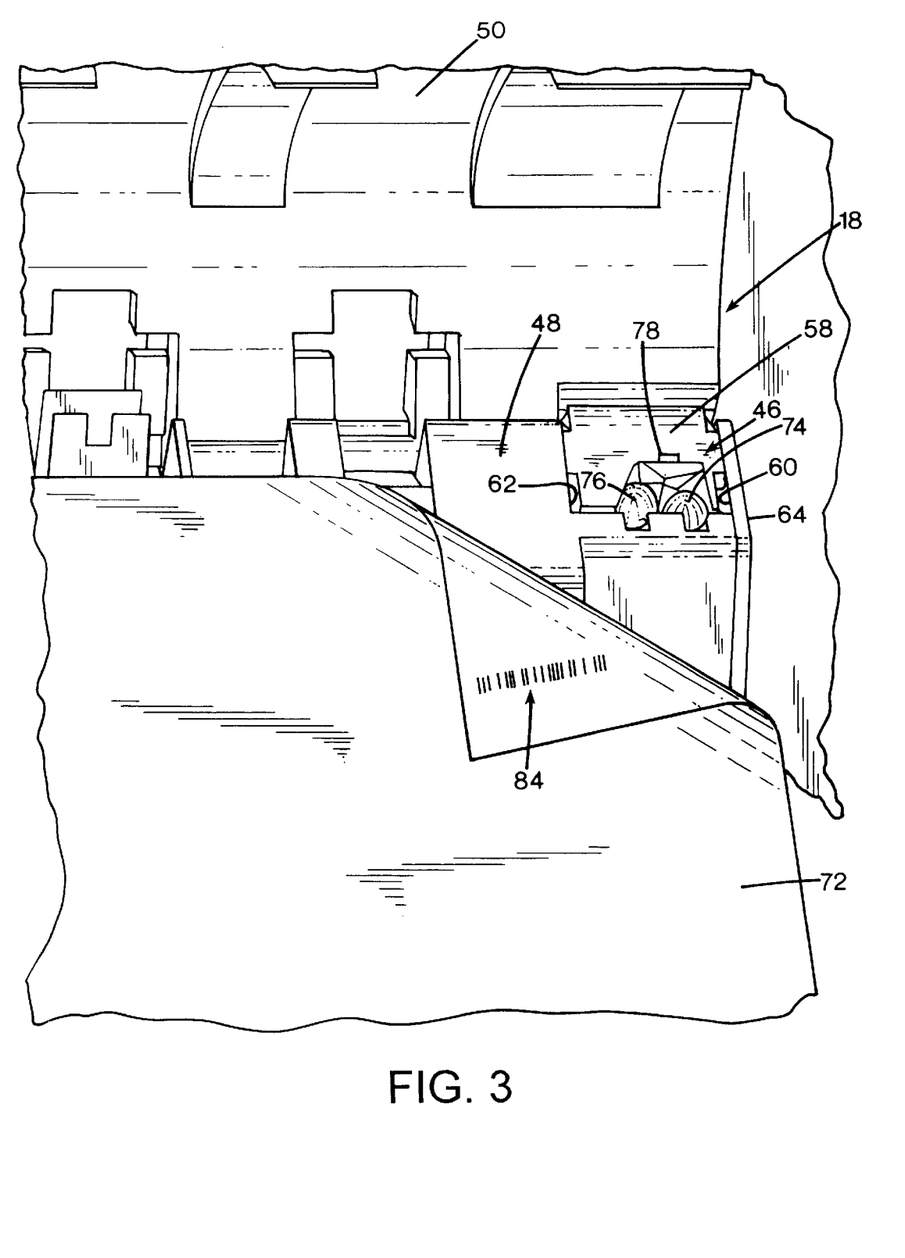
FIG. 3 is an enlarged view of the print media handling system and detector shown in FIG. 2, and a view of a sheet of print media having a pattern of a plurality of marks that indicate at least one characteristic of the sheet of print media

An enlarged view of print media handling system 18 and detector 46 is shown in FIG. 3. Drive rollers 52 and 54 and shaft 56 of print media handling system 18 have been removed for clarity. As can be seen in FIG. 3, detector 46 includes a housing 58 that is secured in lower print media guide 48 inside a recess 60 defined by walls 62 and 64 of lower print media guide 48. Detector 46 is secured within recess 60 by a pair of detents on sides 66 and 68 of housing 58, one of which is shown on side 66 in FIG. 4, an enlarged perspective view of detector 46, by reference numeral 70. Although not shown, it is to be understood that lower print media guide 48 includes a pair of structures such as recesses or hooks that the detents of housing 58 interact with to secure detector 46 within recess 60.

Figure 4:
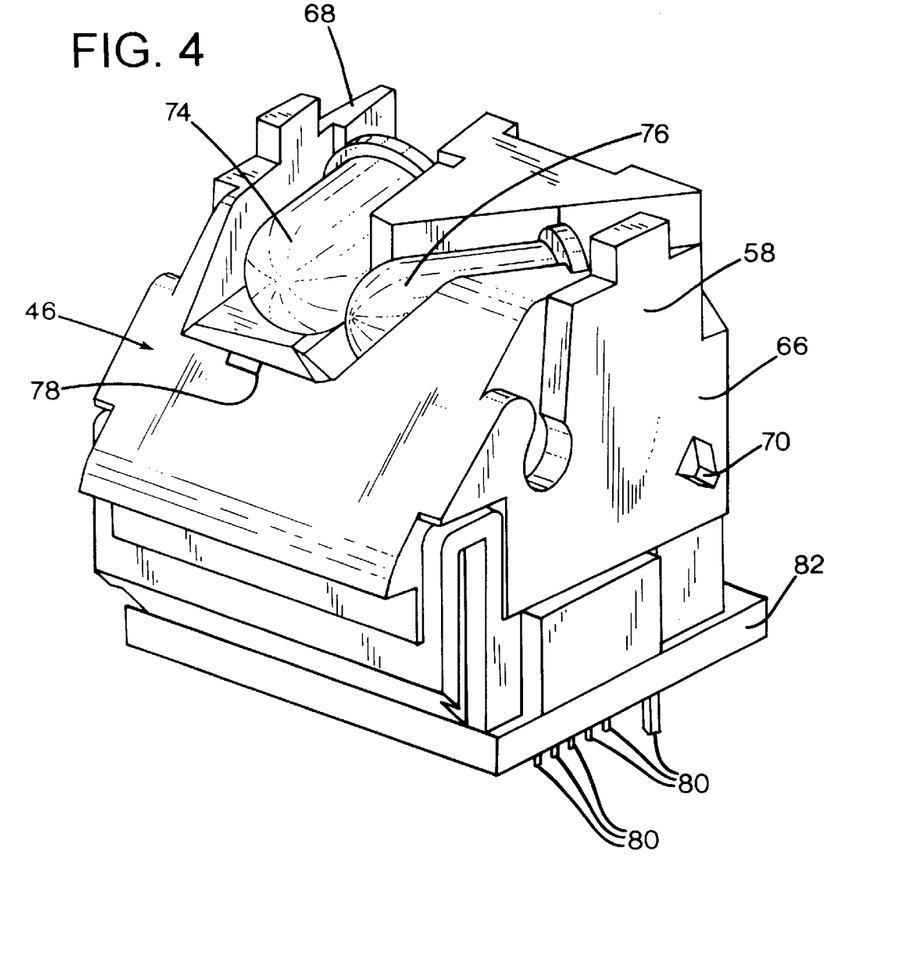
FIG. 4 is an enlarged perspective view of the detector shown in FIGS. 1–3.

As can be seen in FIGS. 3 and 4, detector 46 includes a pair of light emitting diodes (LEDs) 74 and 76 that act as a source of a first light signal that is directed at sheets of print media transported by print media handling system 18 to print zone 16, such as the sheet of print media 72 shown in FIG. 3. LEDs 74 and 76 may emit a single wavelength of light or, alternatively, a range of wavelengths of light. In one embodiment of the present invention, LEDs 74 and 76 emit light in a wavelength range substantially between 610 nanometers and 700 nanometers.

Detector 46 also includes a field stop 78 that defines a lens-free opening having dimensions configured to maximize depth of field of a sensor of detector 46, not shown in FIGS. 3 and 4, with respect to sheets of print media, such as sheet 72 shown in FIG. 3. As can be seen, for example, in FIGS. 3 and 4, the lens-free opening defined by field stop 78 has a substantially rectangular shape. In a preferred embodiment of the present invention, the rectangular shaped opening has dimensions of 0.5 millimeters by 1.5 millimeters.

As can be seen in FIG. 4, detector 46 also includes a plurality of electrical contacts 80 on a base portion 82 of housing 58. Electrical contacts 80 transmit data from detector 46 to controller 30 which is configured to utilize this data in controlling operation of the printing mechanism of printing device 10.

Figure 5:
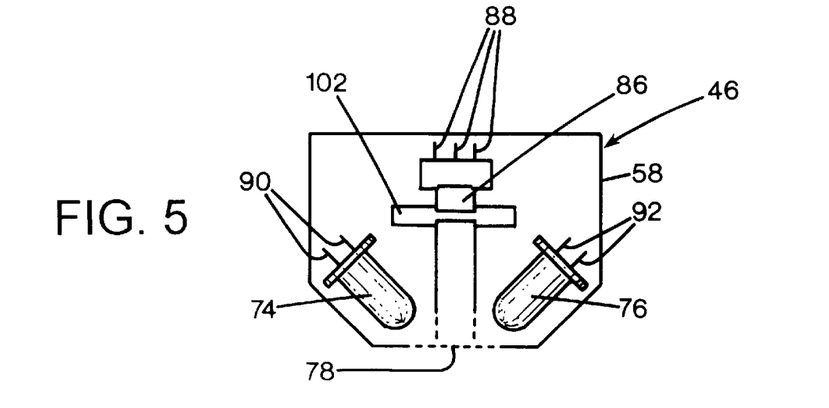
FIG. 5 is a diagrammatic view of the detector shown in FIGS. 1–4.

As can be seen in FIG. 3, sheet of print media 72 includes a pattern 84 thereon, here shown as a plurality of marks arranged in such a manner as to indicate one or more characteristics of the sheet of print media 72. These characteristics may include things such as the type of print media (e.g., paper, transparencies, envelopes, cloth, etc.) and size of sheet 72. As will be more fully discussed below, LEDs 74 and 76 of detector 46 transmit a first light signal that is directed at pattern 84 on print media sheet 72 as print media handling system 18 moves sheet 72 from tray 20 toward print zone 16. In a preferred embodiment of the present invention, pattern 84 consists of a fluorescing ink that absorbs wavelengths of light in the range of the first light signal transmitted by LEDs 74 and 76 and fluoresces a second light signal that passes through field stop 78 and is detected by a sensor 86 (see FIG. 5) of detector 46. In a preferred embodiment of the present invention, sensor 86 is a light-to-voltage optical sensor, manufactured by Texas Instruments under models: TSL 250, TSL 251, and TSL 252. In response to this detection, sensor 86 transmits data indicative of these marks which correspond to at least one characteristic of sheet 72 to controller 30 via terminals 88 which are connected to electrical contacts 80. As can be seen in FIG. 5, LEDs 74 and 76 include respective terminals 90 and 92 which, although not shown in FIG. 5, are also connected to electrical contacts 80 to receive control signals for selective illumination from, for example, controller 30.

Figure 6:
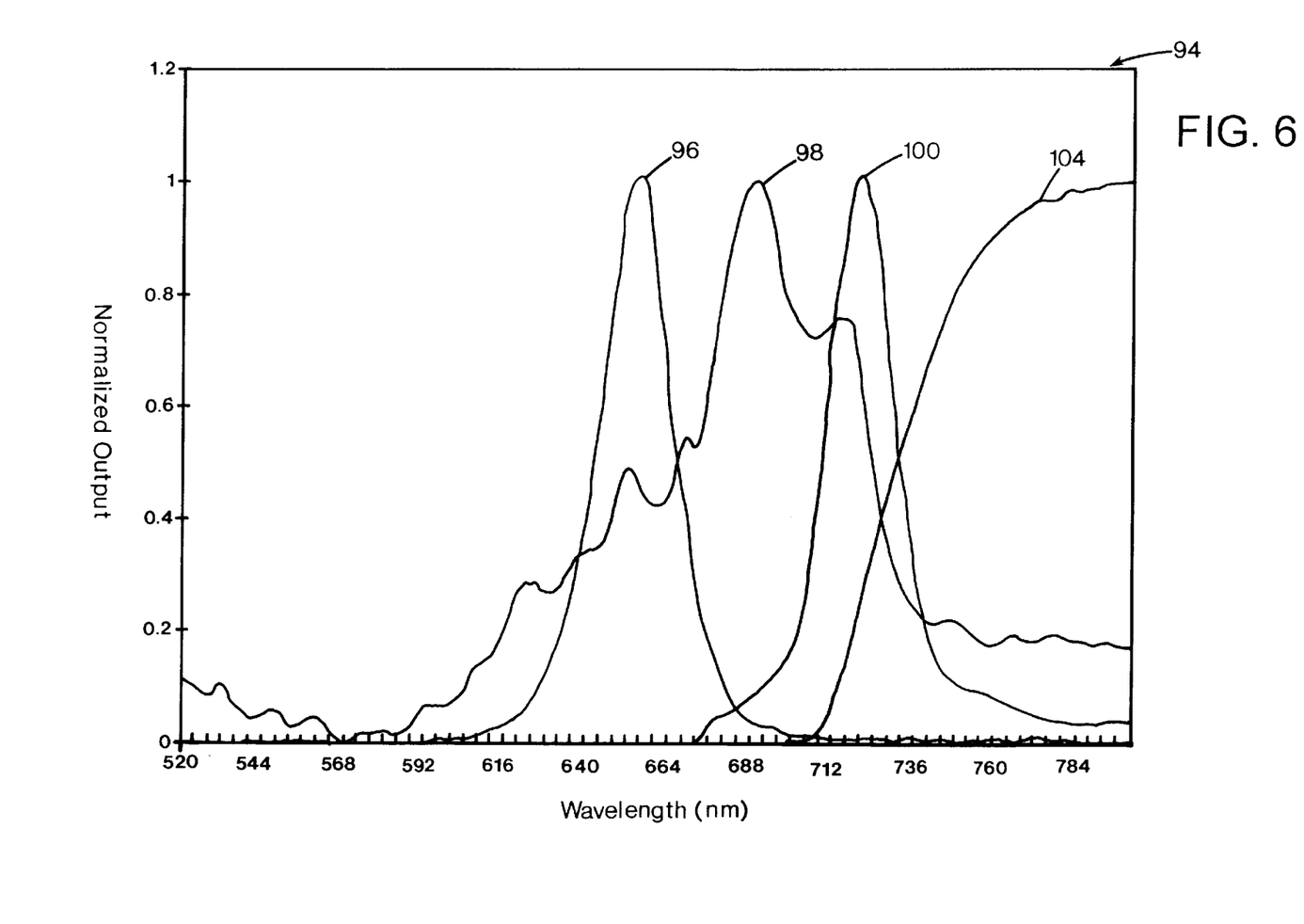
FIG. 6 is a graph of normalized spectra for the detector shown in FIGS. 1–5 and the pattern of a plurality of marks on the print media sheet shown in FIG. 3.

A graph 94 of normalized output spectra versus wavelength for detector 46 and pattern 84 is shown in FIG. 6. Graph 94 includes normalized output spectrum 96 for LEDs 74 and 76, normalized output spectrum 98 for the absorption of the first light signal transmitted by LEDs 74 and 76 by pattern 84, and normalized output spectrum 100 for the second light signal emission by pattern 84. As can be seen in FIG. 6, the wavelength range of output spectrum 96 is substantially between approximately 610 nanometers and 700 nanometers. As can also be seen in FIG. 6, the wavelength range at which marks 84 will absorb light, as represented by curve 98, is within the wavelength range of LEDs 74 and 76 represented by curve 96 in FIG. 6. The marks of pattern 84 fluoresce the above-described second light signal within a wavelength range substantially between approximately 700 nanometers and 785 nanometers, as shown by curve 100. Additional florescence occurs above 785 nanometers, gradually tapering off toward a value of zero from the value shown around 785 nanometers up to approximately 1000 nanometers.

A bandstop filter 102, shown in the diagrammatic view of detector 46 in FIG. 5, is positioned between sensor 86 and field stop 78. Bandstop filter 102 is configured to block wavelengths of light from sensor 86 that are within the range of wavelengths of LEDs 74 and 76 and allows other wavelengths of light to reach sensor 86. The effect of filtering out wavelengths of light from LEDs 74 and 76 allows sensor 86 to detect the fluorescing light signals from the marks of pattern 84 and allows sensor 86 to detect visible inks used in the printing device, the benefit of which is more fully discussed below.

The effect of filtering out wavelengths of light from LEDs 74 and 76 additionally gives sensor 86 an improved signal-to-noise ratio. When detector 46 is not over pattern 84, only a very small amount of ambient light reaches sensor 86, resulting from such things as leakage through the filter and ambient light. This provides a very low noise base line. When detector 46 is adjacent pattern 84, the florescent ink thereof emits a strong light source, in this case, the above-described second light signal, which produces high contrast to dark areas where no florescent ink is located. This high contrast allows the ink used to create pattern 84 to be applied in very low concentrations which makes them less visible to the eye.

As discussed above, in addition to accounting for particular media types, there are various operating parameters of a printing device that must be initialized and monitored to help achieve optimal printing. With inkjet printing devices, such as inkjet printer 10, some of these parameters include alignment of a black ink cartridge with one or more color ink cartridges, detection of clogged printhead nozzles, ink drop volume measurement, and bi-directional printing alignment.

One way in which these various tasks can be accomplished for inkjet printing is through the use of a optical detector, such as detector 46, that includes a sensor, such as sensor 86, which is configured to detect visible inks used in printing device 10. Detector 46 is designed to transmit data acquired by this detection to controller 30 which utilizes this data in managing operation of inkjet printer 10.

Figure 7:
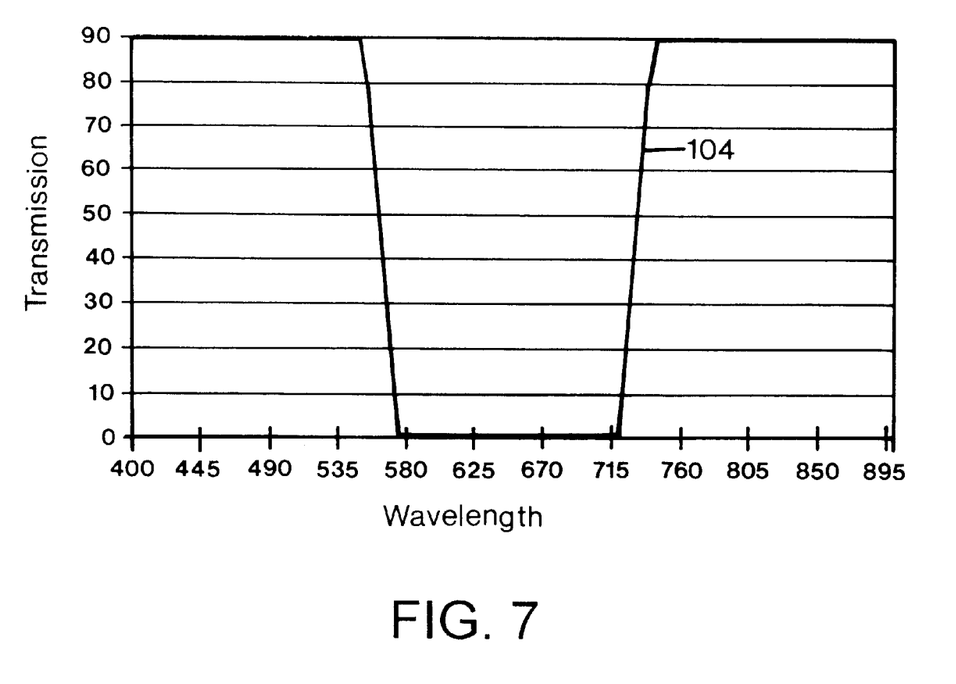
FIG. 7 is a curve which represents the normalized transmission wavelength spectrum for a bandstop filter in accordance with the present invention.

A curve 104 is shown in FIG. 7 which represents the normalized transmission wavelength spectrum for bandstop filter 102. As can be seen in FIG. 7, the normalized transmission wavelength spectrum of bandstop filter 102 represented by curve 104 blocks light in a wavelength range approximately between 575 nanometers and 720 nanometers. Thus, bandstop filter 102 blocks substantially all of the first light signal from LEDs 74 and 76 but allows a significant portion of the second light signal from the marks of pattern 84 represented by curve 100 to reach sensor 86. Additionally, bandstop filter 102 allows wavelengths of light from inks used by printing device 10 in the visible spectrum below approximately 575 nanometers to reach sensor 86 for detection thereof and use in managing operation of inkjet printer 10, as discussed above. Bandstop filter 102 further allows wavelengths of light above approximately 720 nanometers to reach sensor 86 for detection thereof and use in other potential applications.

Although particular wavelength ranges have been represented for the various normalized spectra shown in FIGS. 6 and 7, it is to be understood that it is within the scope of the present invention to modify one or more of theses wavelength ranges as needed. In addition, it is to be understood that in alternative embodiments of the present invention, the normalized output magnitudes for the various output spectra shown in FIG. 6 may vary as well, as may the transmission percentage of bandstop filter 102 shown in FIG. 7. For example, an alternative embodiment of a bandstop filter in accordance with the present invention may transmit greater than approximately 90% of light outside of the blocking range. However, such filters are usually more difficult to manufacture and, consequently, are more expensive.

Figure 8:
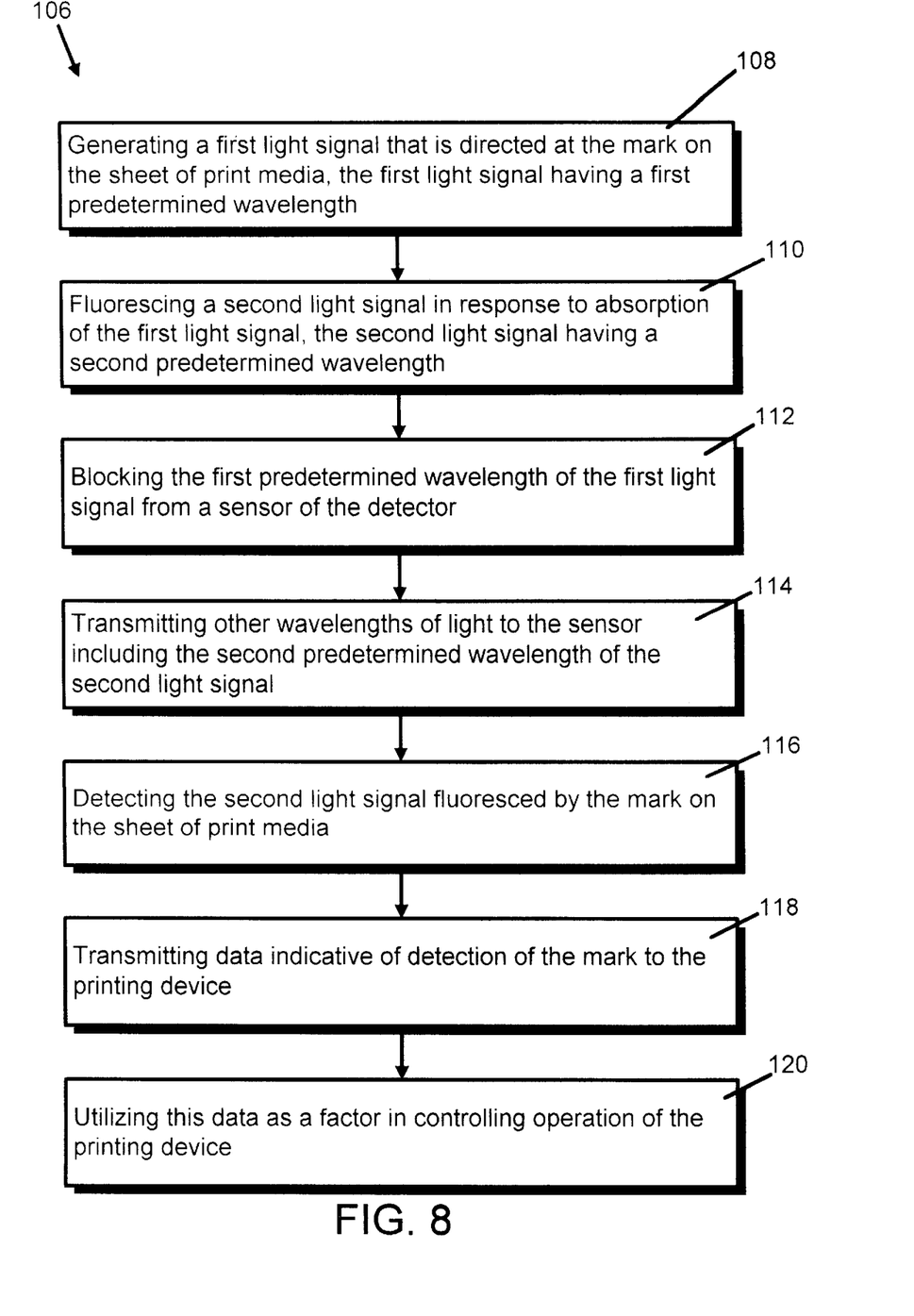
FIG. 8 is a diagram of an embodiment of a method in accordance with the present invention.

A diagram of a method 106 of detecting a characteristic of a sheet of print media used in a printing device through the use of a detector in accordance with the present invention is shown in FIG. 8. Method 106 includes the step of generating a first light signal that is directed at the mark on the sheet of print media 108. This first light signal has a first predetermined wavelength. Method 106 additionally includes the step 110 of fluorescing a second light signal in response to absorption of the first light signal. The second light signal has a second predetermined wavelength. Method 106 additionally includes the steps of blocking the first predetermined wavelength of the first light signal from the sensor of the detector 112 and transmitting other wavelengths of light to the sensor including the second predetermined wavelength of the second light signal 114. Method 106 additionally includes the step 116 of detecting the second light signal fluoresced by the mark on the sheet of print media.

The first light signal may have a first range of predetermined wavelengths and the second light signal may also have a second range of predetermined wavelengths. In these cases, the blocking step includes blocking the first range of predetermined wavelengths of the first light signal. In these cases, the transmitting step includes transmitting other wavelengths of light, including the second range of predetermined wavelengths of the second light signal.

As shown in FIG. 8, method 106 may additionally include the step 118 of transmitting data indicative of detection of the mark to the printing device and the step 120 of utilizing this data as a factor in controlling operation of the printing device.

Although the invention has been described and illustrated in detail, it is to be clearly understood that the same is intended by way of illustration and example only, and is not to be taken necessarily, unless otherwise stated, as an express limitation. For example, LEDs 74 and 76 may be combined into a single LED as the source of the first light signal. As another example, LEDs 74 and 76 may be designed to emit different wavelengths of light, one for media detection and the other for ink detection, as discussed above. In such embodiments, bandstop filter 102 may need to be modified so as to block a different range of wavelengths of light to account for the change of LEDs 74 and 76. As a further example, in other embodiments of the present invention, sensor 86 and bandstop filter 102 may be integrated into a single structure. Furthermore, although specific quantities and ranges have been given, it is to be understood that other quantities and ranges are within the scope of the present invention. The spirit and scope of the present invention are to be limited only by the terms of the following claims.

What is claimed is:

1. A printing device, comprising:
   a sheet of print media having at least one mark thereon that indicates a characteristic of the sheet of print media, the mark fluorescing at a second predetermined wavelength of light in response to absorption of a first light signal of a first predetermined wavelength;
   a printing mechanism for printing on the sheet of print media;
   a controller that controls operation of the printing mechanism; and
   a detector that detects fluorescing of the mark on the sheet of print media and transmits in response to this detection data indicative of this mark to the controller, the detector including a bandstop filter that is configured to block the first predetermined wavelength of the first light signal and to transmit other wavelengths of light, including the second predetermined wavelength of the second light signal;
   wherein the controller is configured to utilize this data as a factor in controlling operation of the printing mechanism.

2. The printing device of claim 1, wherein the first light signal has a first range of predetermined wavelengths and the second light signal has a second range of predetermined wavelengths, and further wherein the bandstop filter is configured to block the first range of predetermined wavelengths of the first light signal and transmit other wavelengths of light, including the second range of predetermined wavelengths of the second light signal.

3. The printing device of claim 2, wherein the first range of wavelengths is substantially between 610 nanometers and 700 nanometers, and further wherein the second range of wavelengths is substantially between 675 nanometers and 1000 nanometers.

4. The printing device of claim 1, further comprising a source configured to transmit the first light signal toward the sheet of print media.

5. A detector for use in detecting at least one mark on a sheet of print media used in a printing device, the mark indicating at least one characteristic of the sheet of print media, the detector comprising:
   a source that generates a first light signal that is directed at the mark on the sheet of print media, the first light signal having a first predetermined wavelength;
   a sensor configured to detect a second light signal from the mark on the sheet of print media, the second light signal arising in response to the first light signal and having a second predetermined wavelength; and
   a bandstop filter positioned between the sensor and the mark on the sheet of print media, the bandstop filter being configured to block from the sensor the first predetermined wavelength of the first light signal generated by the source and transmit to the sensor other wavelengths of light, including the second predetermined wavelength of the second light signal.

6. The detector of claim 5, wherein the first light signal has a first range of predetermined wavelengths and the second light signal has a second range of predetermined wavelengths, and further wherein the bandstop filter is configured to block from the sensor the first range of predetermined wavelengths of the first light signal and transmit other wavelengths of light to the sensor, including the second range of predetermined wavelengths of the second light signal.

7. The detector of claim 6, wherein the first range of wavelengths is substantially between 610 nanometers and 700 nanometers, and further wherein the second range of wavelengths is substantially between 675 nanometers and 1000 nanometers.

8. The detector of claim 5, in a printing device.

9. A detector for use in detecting at least one mark on a sheet of print media used in a printing device, the mark indicating at least one characteristic of the sheet of print media, the detector comprising:
   means for generating a first light signal that is directed at the mark on the sheet of print media, the first light signal having a first predetermined wavelength;
   means for detecting a second light signal from the mark on the sheet of print media, the second light signal arising in response to the first signal and having a second predetermined wavelength; and
   means, positioned between the means for detecting and the mark on the sheet of print media, for blocking from the means for detecting the first predetermined wavelength of the first light signal and for transmitting to the means for detecting other wavelengths of light, including the second predetermined wavelength of the second light signal, thereby allowing wavelengths of light other than the first wavelength of light to remain available for tasks other than detecting the mark on the sheet of print media.

10. The detector of claim 9, wherein the first light signal has a first range of predetermined wavelengths and the second light signal has a second range of predetermined wavelengths, and further wherein the means for blocking and transmitting is configured to block from the means for detecting the first range of predetermined wavelengths of the first light signal and transmit to the means for detecting other wavelengths of light, including the second range of predetermined wavelengths of the second light signal.

11. The detector of claim 10, wherein the first range of wavelengths is substantially between 610 nanometers and 700 nanometers, and further wherein the second range of wavelengths is substantially between 675 nanometers and 1000 nanometers.

12. The detector of claim 9, wherein the means for blocking and transmitting includes a bandstop filter positioned between the means for detecting and the mark on the sheet of print media.

13. The detector of claim 12, wherein the first light signal has a first range of predetermined wavelengths and the second light signal has a second range of predetermined wavelengths, and further wherein the bandstop filter is configured to block from the means for detecting the first range of predetermined wavelengths of the first light signal and transmit other wavelengths of light to the means for detecting, including the second range of predetermined wavelengths of the second light signal.

14. The detector of claim 13, wherein the first range of wavelengths is substantially between 610 nanometers and 700 nanometers, and further wherein the second range of wavelengths is substantially between 675 nanometers and 1000 nanometers.

15. The detector of claim 9, wherein the means for generating includes a light emitting diode and the means for detecting includes an optical detector.

16. The detector of claim 9, in a printing device.

17. A method of detecting a characteristic of a sheet of print media used in a printing device through the use of a detector, the method comprising the steps of:

generating a first light signal that is directed at the mark on the sheet of print media, the first light signal having a first predetermined wavelength;

fluorescing a second light signal in response to absorption of the first light signal, the second light signal having a second predetermined wavelength;

blocking the first predetermined wavelength of the first light signal from a sensor of the detector;

transmitting other wavelengths of light to the sensor including the second predetermined wavelength of the second light signal; and detecting the second light signal fluoresced by the mark on the sheet of print media.

18. The method of claim 17, wherein the first light signal has a first range of predetermined wavelengths and the second light signal has a second range of predetermined wavelengths, and further wherein the blocking step includes blocking the first range of predetermined wavelengths of the first light signal and the transmitting step includes transmitting other wavelengths of light, including the second range of predetermined wavelengths of the second light signal.

19. The method of claim 17, further comprising the steps of:

transmitting data indicative of detection of the mark to the printing device; and utilizing this data as a factor in controlling operation of the printing device.

* * * * *